United States Patent
Nakajima (10) Patent No.: US 8,857,993 B2
(45) Date of Patent: Oct. 14, 2014

(54) OPHTHALMOLOGIC APPARATUS (75) Inventor: Hajime Nakajima, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 204 days.

(21) Appl. No.: 13/557,081

(22) Filed: Jul. 24, 2012

(65) Prior Publication Data

US 2013/0027669 A1  Jan. 31, 2013

(30) Foreign Application Priority Data

Jul. 29, 2011  (JP) .................................. 2011-167056

(51) Int. Cl.
A61B 3/00 (2006.01)

(52) U.S. Cl.
CPC .................................... *A61B 3/0075* (2013.01)
USPC ......................................................... 351/245

(58) Field of Classification Search
CPC .................................................... A61B 3/0075
USPC ......................................................... 351/245
See application file for complete search history.

(56) References Cited

U.S. PATENT DOCUMENTS

| 5,406,076 A | 4/1995 | Mimura |
| 5,502,519 A | 3/1996 | Hosoi |
| 6,439,719 B2 * | 8/2002 | Hayashi et al. ............... 351/208 |

FOREIGN PATENT DOCUMENTS

| CN | 001272050 A | 11/2000 |
| CN | 001989894 A | 7/2007 |
| CN | 101322643 A | 12/2008 |
| CN | 101410047 A | 4/2009 |
| EP | 1803390 A2 | 7/2007 |
| JP | H02-193636 A | 7/1990 |
| JP | 03-026228 A | 2/1991 |
| JP | H03-261449 A | 11/1991 |
| JP | H09-224911 A | 9/1997 |
| JP | 2003-275177 A | 9/2003 |

* cited by examiner

*Primary Examiner* — Huy K Mai
(74) *Attorney, Agent, or Firm* — Canon USA Inc IP Division (57) ABSTRACT

An ophthalmologic apparatus including a measurement unit configured to measure a subject's eye, a sliding substrate configured to slide the measurement unit with respect to a base via a guide shaft, a plurality of shaft guide members provided on the base and configured to guide the guide shaft in an axial direction thereof, and an inclination reduction unit provided between the plurality of shaft guide members and configured to reduce inclination of the guide shaft with respect to the base.

14 Claims, 8 Drawing Sheets

OPHTHALMOLOGIC APPARATUS

BACKGROUND OF THE INVENTION

1. Field of the Invention

The present invention relates to an ophthalmologic apparatus that includes a mechanism for sliding a sliding substrate having an optical system unit, such as a fundus camera or an ophthalmoscope, on a horizontal plane.

2. Description of the Related Art

Conventionally, an ophthalmologic apparatus has been configured by mounting a sliding substrate, which can slide in forward/backward and lateral directions in response to an operation made by an operation stick, on a fixed base to which a face receiving portion for a subject is attached. In such an ophthalmologic apparatus, an optical system main unit is mounted on the sliding substrate via a vertical motion mechanism.

Japanese Patent Application Laid-Open No. 03-026228 discusses an ophthalmologic apparatus in which a guide tube and a guide shaft are arranged between a sliding substrate and a fixed base, so that the sliding substrate moves in a lateral direction with respect to the fixed base by sliding the guide shaft through the guide tube. Further, a pinion gear attached to both ends of the guide shaft engages with a rack that is arranged on either side of the sliding substrate. The sliding substrate on which the rack that engages with the pinion gear is arranged moves in a forward/backward direction with respect to the fixed base by rotating the pinion gear in synchronization with the guide shaft.

Further, a ball bearing is attached at a position near the pinion gear on either end of the guide shaft. The ball bearing allows the guide shaft to smoothly rotate by maintaining a gap that is suitable for the engagement between the pinion gear and the rack while supporting the weight of the sliding substrate via the guide face of the sliding substrate. In this case, the ball bearing acts as a mechanism for preventing the sliding substrate from lifting up from the fixed base by stopping a rack gear plate from lifting up from the guide shaft.

However, uplift of the sliding substrate from the fixed base is also caused by inclination of the guide shaft with respect to the guide tube attached to an upper portion of the fixed base. For example, when a subject's eye is to be aligned with the ophthalmologic apparatus, the sliding substrate may be moved in a lateral direction (axial direction of the guide shaft). In such a case, if the distance between the guide tube and the guide shaft's center of gravity increases, the difference in the moments acting on the two ends of the guide shaft increases. Consequently, the guide shaft is more likely to incline with respect to the guide tube.

SUMMARY OF THE INVENTION

The present invention is directed to an ophthalmologic apparatus capable of reducing the inclination of a guide shaft with respect to a shaft guide member by providing an inclination reduction unit between a plurality of shaft guide members that are arranged on a base and that guide the guide shaft in an axial direction thereof.

According to an aspect of the present invention, an ophthalmologic apparatus includes a measurement unit configured to measure a subject's eye, a sliding substrate configured to slide the measurement unit with respect to a base via a guide shaft, a plurality of shaft guide members provided on the base and configured to guide the guide shaft in an axial direction thereof, and an inclination reduction unit provided between the plurality of shaft guide members and configured to reduce inclination of the guide shaft with respect to the base.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Figure 2:
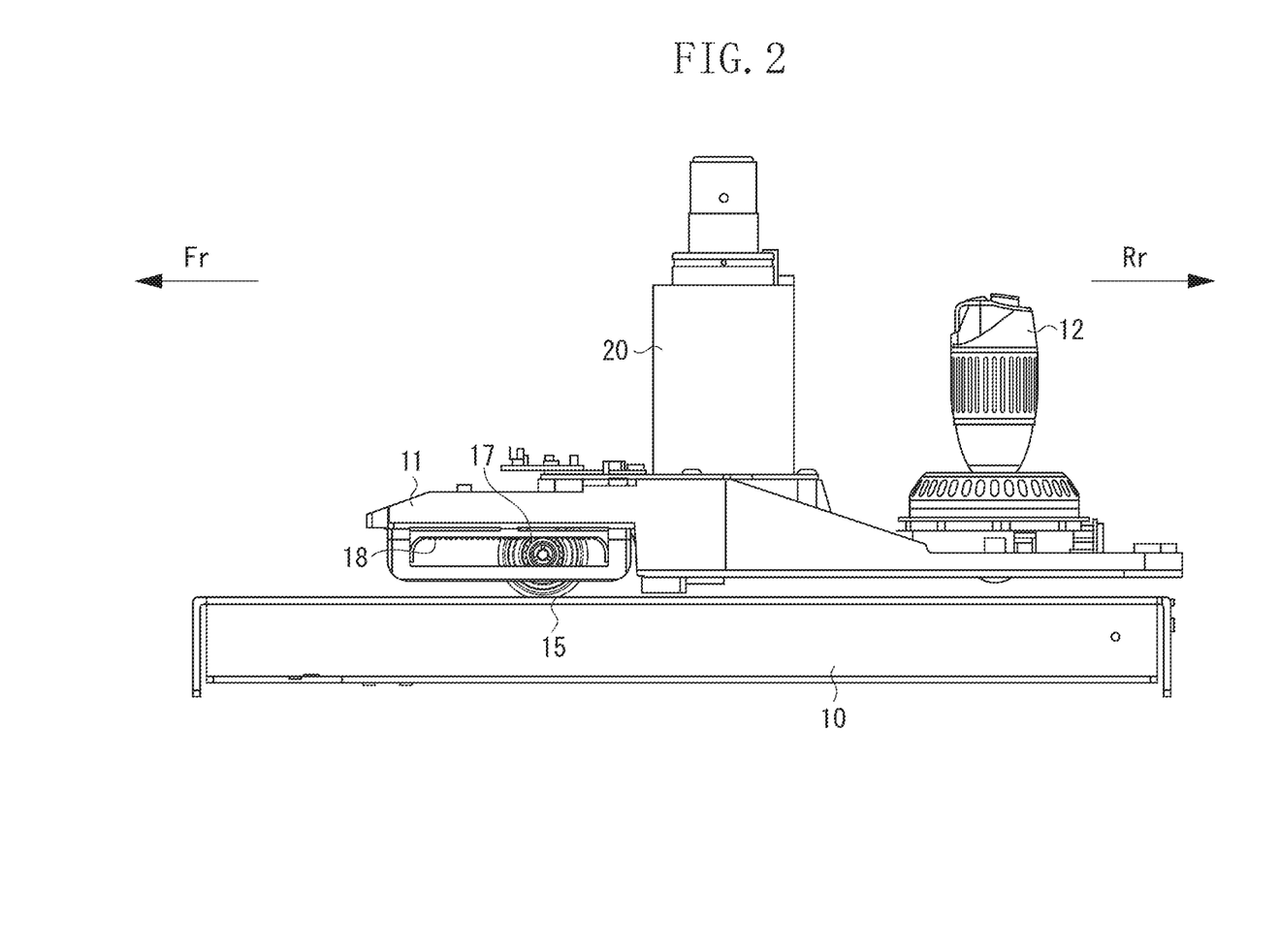
FIG. 2 is a side view illustrating the ophthalmologic apparatus according to an exemplary embodiment of the present invention, from which a portion of the housing has been removed.
Figure 3:
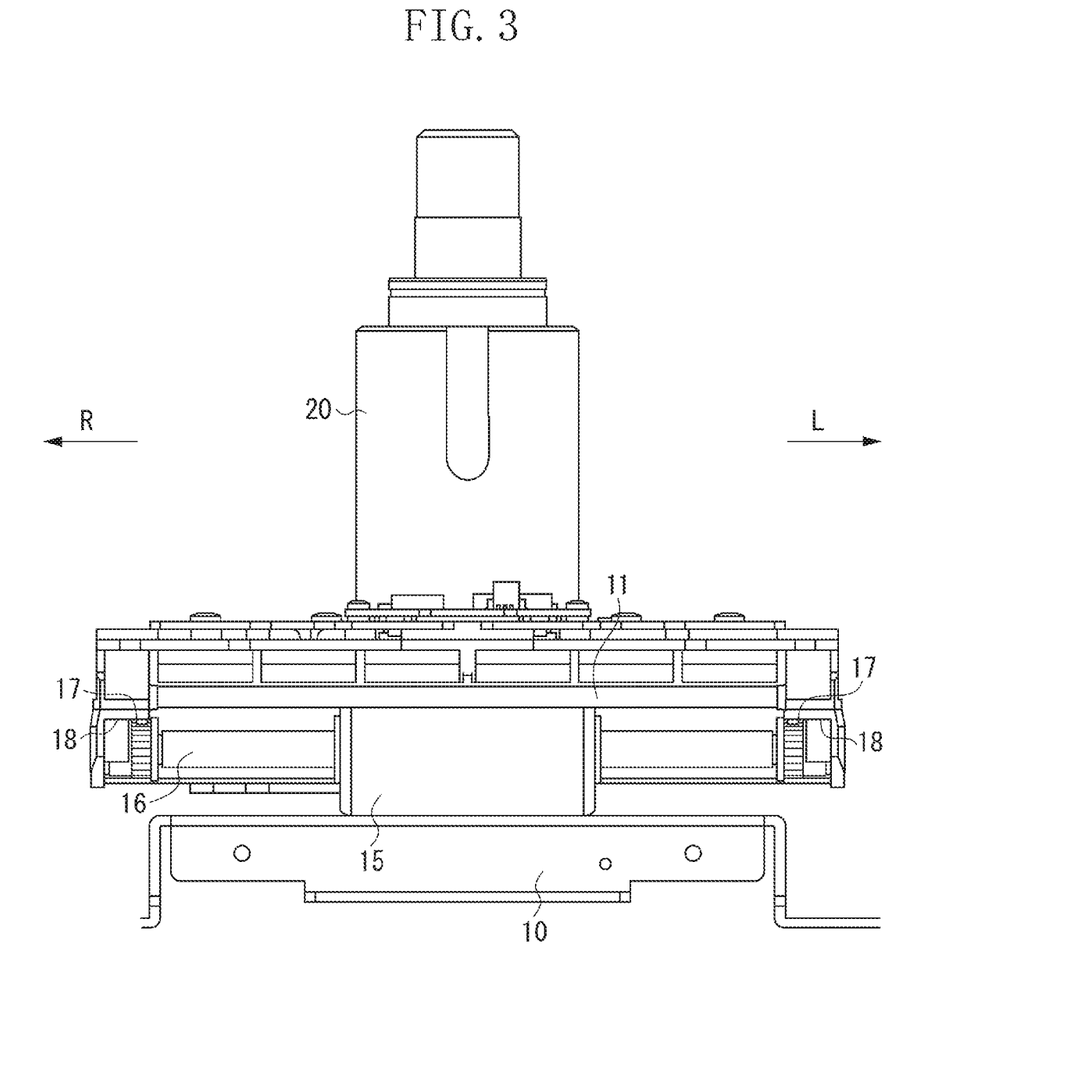
FIG. 3 is a front view illustrating the ophthalmologic apparatus according to an exemplary embodiment of the present invention, from which a portion of the housing has been removed.

First, the general configuration of the ophthalmologic apparatus according to an exemplary embodiment of the present invention will be described with reference to FIGS. 1 to 3.

Figure 1:
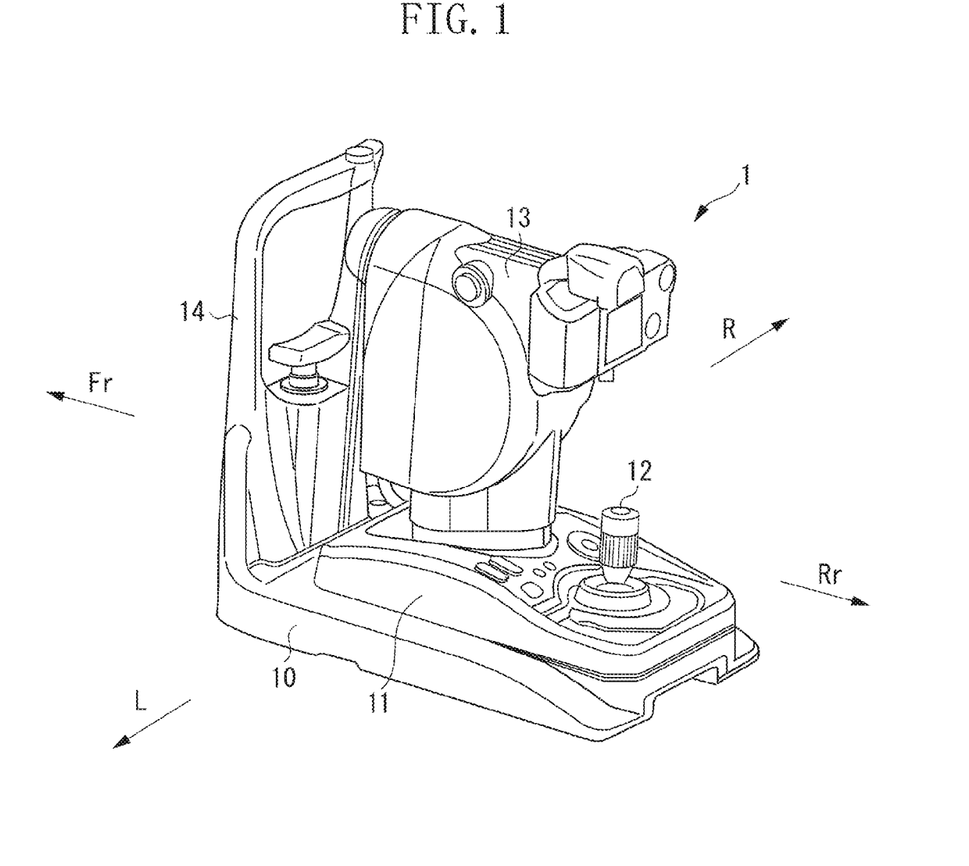
FIG. 1 illustrates an overall configuration of an ophthalmologic apparatus according to an exemplary embodiment of the present invention.

FIG. 1 is a perspective view illustrating the overall configuration of an ophthalmologic apparatus. FIG. 2 is a side view illustrating the ophthalmologic apparatus, from which a portion of the housing has been removed. FIG. 3 is a front view illustrating the ophthalmologic apparatus, from which a portion of the housing has been removed. In the respective figures, as necessary, the front side of the ophthalmologic apparatus is denoted as Fr, the rear side is denoted as Rr, the right side is denoted as R, and the left side is denoted as L.

First, as illustrated in FIG. 1, an ophthalmologic apparatus 1 is configured from a fixed base 10 (also referred to as a "base"), a sliding substrate 11, an operation stick 12, an optical system unit 13, and a face receiving portion 14. The housing (also referred to as a "measuring unit for measuring a subject's eye") of the fixed base 10, the sliding substrate 11, and the optical system unit 13 are formed from a resin molded article to make the ophthalmologic apparatus 1 lighter.

The ophthalmologic apparatus 1 is configured so that the sliding substrate 11 can be moved forward/backward and laterally with respect to the fixed base 10 in response to an operation by the operator using the operation stick 12. If movement of the sliding substrate 11 is electrically controlled, it is desirable for the control to be performed in cooperation with operation of the operation stick 12 by a (not illustrated) control unit. As illustrated in FIGS. 2 and 3, the sliding substrate 11 is provided on the fixed base 10 via a horizontal motion mechanism 15. The horizontal motion mechanism 15 supports a guide shaft 16 erected in a lateral direction at a lower side of the sliding substrate 11 so that the guide shaft 16 can slide in an axial direction thereof and rotate in a circumferential direction. The horizontal motion mechanism 15 slides the guide shaft 16, so that the sliding substrate 11 slides in the lateral direction (X direction) with respect to the fixed base 10. The configuration of the horizontal motion mechanism 15 will be described in more detail below.

A rack and pinion mechanism (also referred to as a "movement unit for moving the sliding substrate in a forward/backward direction with respect to the fixed base") is provided on both sides of the guide shaft 16. Specifically, a pinion gear 17 (also referred to as a "pinion mechanism") is fixed on both sides of the guide shaft 16. The pinion gears 17 engage with a rack 18a formed on a rack gear plate 18 (also referred to as a "rack mechanism") that is fixed on the sliding substrate 11. The horizontal motion mechanism 15 rotates the guide shaft 16 in one direction, so that the position where the guide shaft 16 and the rack 18a engage changes, and the sliding substrate 11 slides in the forward/backward direction (Z direction, i.e., the direction that intersects the axial direction of the guide shaft 16) with respect to the fixed base 10. The configuration for making the sliding substrate 11 slide with respect to the fixed base 10 will be described in more detail below.

The operation stick 12 arranged at a rear side of the sliding substrate 11 has a (not illustrated) hard ball provided on its lower end. The hard ball presses against a (not illustrated) friction plate that is fixed on the fixed base 10, while accepting a part of the weight of the sliding substrate 11.

In the thus-configured ophthalmologic apparatus 1, when the operator inclines the operation stick 12 in the lateral direction, the guide shaft 16 supported by the horizontal motion mechanism 15 moves horizontally along the axial direction regardless without rotating, so that the sliding substrate 11 moves in the lateral direction (X direction) with respect to the fixed base 10.

When the operator inclines the operation stick 12 in the forward/backward direction, the guide shaft 16 supported by the horizontal motion mechanism 15 rotates. The pinion gear 17 rotates in synchronization with the rotation of the guide shaft 16, so that the sliding substrate 11 moves in the forward/backward direction (Z direction) with respect to the fixed base 10.

Further, a vertical motion mechanism 20 is arranged on the sliding substrate 11. The vertical motion mechanism 20 moves the optical system unit 13 in a vertical direction (Y direction) with respect to the fixed base 10 and the sliding substrate 11.

Figure 4:
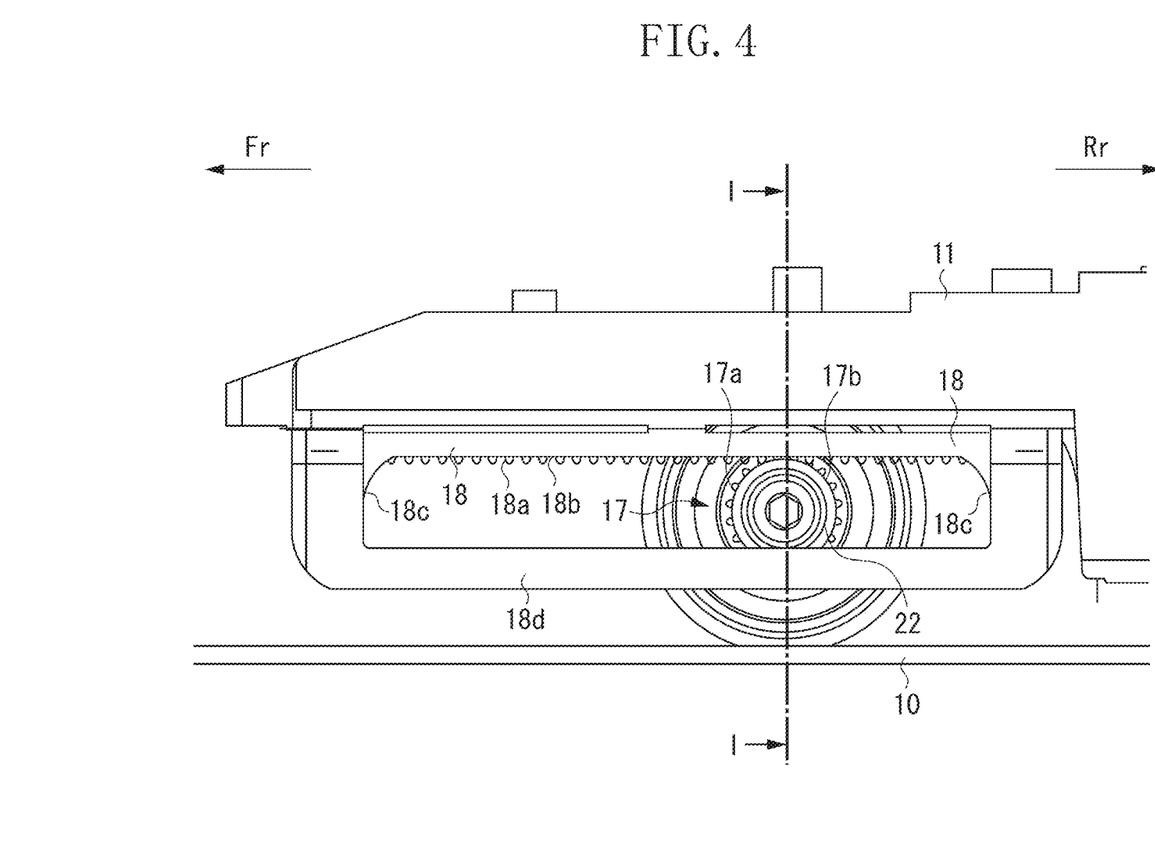
FIG. 4 is a side view of a sliding mechanism according to an exemplary embodiment of the present invention.
Figure 5:
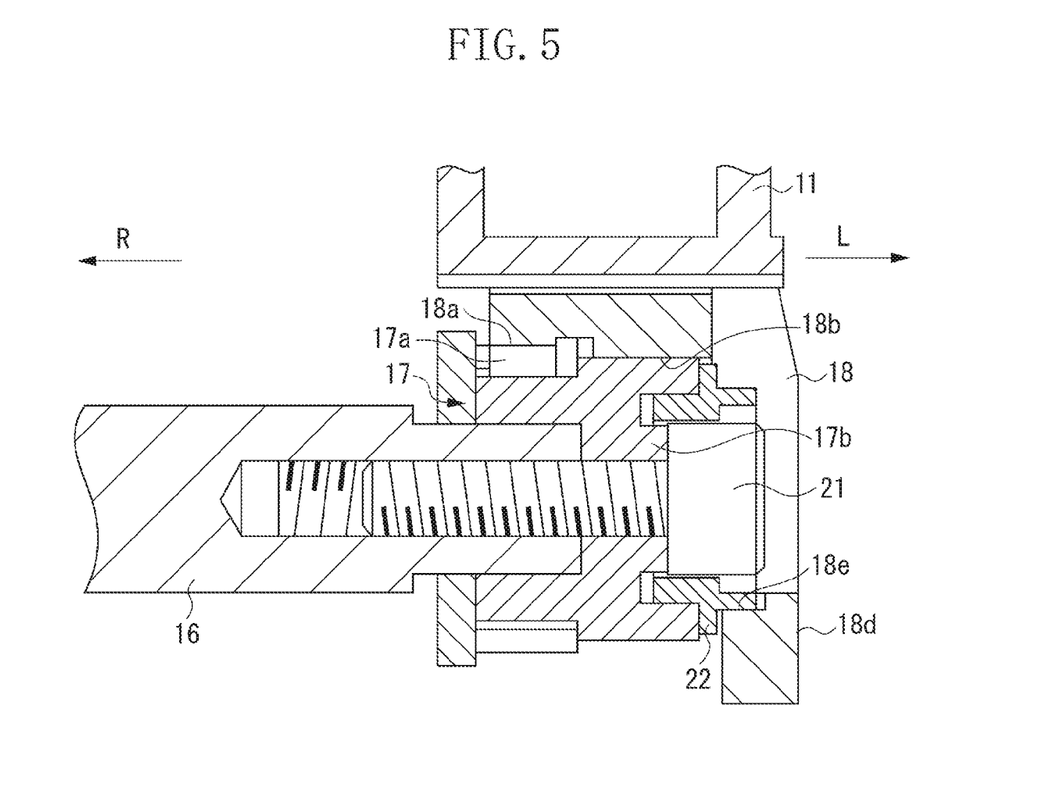
FIG. 5 is a cross-sectional view of the sliding mechanism according to an exemplary embodiment of the present invention.

Next, the sliding mechanism that slides the sliding substrate 11 with respect to the fixed base 10 will be described in more detail with reference to FIGS. 4 and 5. FIG. 4 is an enlarged side view of the sliding mechanism. FIG. 5 is a cross-sectional view along the line I-I illustrated in FIG. 4 as viewed in the arrow direction. Although only the left side of the guide shaft is illustrated in FIGS. 4 and 5, the right side also has the same configuration.

As illustrated in the cross-sectional of FIG. 5, the pinion gear 17 is fixed to an end of the guide shaft 16 by a fixing bolt 21 that is screwed into the end face of the guide shaft 16. Therefore, the guide shaft 16 and the pinion gear 17 always rotate in synchronization. Further, a pinion member 17a is formed on the pinion gear 17 on an inner side in the axial direction, and a roller member 17b acting as a guided member is formed on the pinion gear 17 on an outer side in the axial direction. The pinion member 17a engages with the rack 18a of the rack gear plate 18. In addition, an outer periphery of the cylindrical roller member 17b is in contact with a below-described roller guide face 18b arranged on the sliding substrate 11.

An uplift prevention washer 22 is rotatably fitted to the guide shaft 16 on an outer end of the pinion gear 17 which is at the end of the guide shaft 16. Specifically, the uplift prevention washer 22 is sandwiched between the outer periphery of the top portion of the fixing bolt 21 and the inner periphery of the pinion gear 17. In a case where the sliding substrate 11 is lifted up due to a movement in the center of gravity of the sliding substrate 11, the uplift prevention washer 22 regulates the lifting up of the sliding substrate 11 by abutting a below-described washer guide face 18c formed parallel to the roller guide face 18b of the rack gear plate 18.

The rack gear plate 18 is fixed along the sliding direction (forward/backward direction) of the sliding substrate 11 on a lower face of the left and right ends of the sliding substrate 11. On the rack gear plate 18 are formed the rack 18a that engages with the pinion member 17a and the roller guide face 18b acting as a guided member that is in contact with the roller member 17b. The roller guide face 18b is formed on an outer side of the rack 18a parallel to the rack 18a. By guiding the roller member 17b in the sliding direction with the roller guide face 18b, the relative movement between the sliding substrate 11 and the fixed base 10 is stabilized. Further, by bringing the roller member 17b and the roller guide face 18b into contact with each other, the roller member 17b can support a part of the weight of the sliding substrate 11, so that the engagement between the pinion member 17a of the pinion gear 17 and the rack 18a is supported at an appropriate interval.

A stopper 18c is formed respectively near the front and rear terminal portions (front and rear ends) of the rack 18a. By abutting the roller member 17b of the pinion gear 17 against the stoppers 18c, the movement amount of the sliding substrate 11 in the forward/backward direction is regulated.

The rack gear plate 18 is formed with a suspension member 18d that protrudes downward from the respective front and rear stoppers 18c and bridges across the space between them. On an upper face of the suspension member 18d, a washer guide face 18e is formed that abuts the uplift prevention washer 22.

Figure 6A:
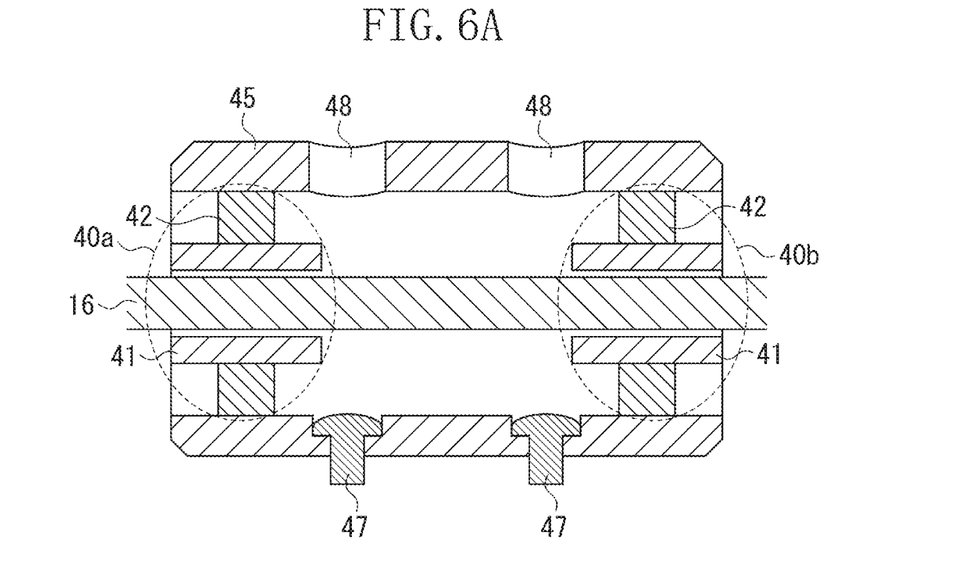
FIGS. 6A, 6B, and 6C are cross-sectional views of a horizontal motion mechanism and an inclination reduction unit according to an exemplary embodiment of the present invention.

The configuration of the horizontal motion mechanism 15 according to the present exemplary embodiment will now be described in more detail with reference to FIG. 6A. FIG. 6A is a cross-sectional view illustrating the horizontal motion mechanism 15 according to the present exemplary embodiment.

The horizontal motion mechanism 15 according to the present exemplary embodiment is a mechanism that supports the guide shaft 16 with a plurality of shaft guide members 40a and 40b (also referred to as a "first shaft guide unit") that fit a rolling bearing 42 (e.g., a deep-groove spherical bearing, a ball bearing, a needle-shaped rolling bearing, or a needle bearing) on the outer periphery of a linear motion bearing 41 (e.g., a slide bearing or a linear bush) arranged in a storage unit 45. In this case, the guide shaft 16 is configured so that it can rotate in an axial direction thereof via the linear bearing 41. Further, the guide shaft 16 is also configured so that it can rotate via the rolling bearing 42. It is desirable to use a screw 47 to fix the horizontal motion mechanism 15 to the fixed base 10. In this case, it is desirable to open a hole 48 on an upper portion of the storage unit 45. Since the screw 47 can be rotated with a driver, for example, through the hole 48, the horizontal motion mechanism 15 can be easily fixed to the fixed base 10.

Figure 7A:
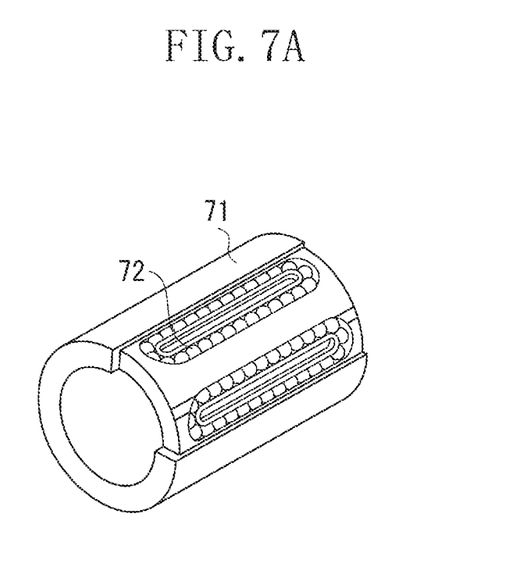
FIGS. 7A and 7B are schematic diagrams illustrating an example of a linear motion bearing and a rolling bearing according to an exemplary embodiment of the present invention.

An example of the linear motion bearing 41 according to the present exemplary embodiment will now be described using FIG. 7A. A linear motion bearing is a bearing that moves linearly in the axial direction of the guide shaft 16. A plurality of balls 72 provided in a plurality of grooves in an outer casing 71 roll in a straight line (orderly cyclic motion) while receiving a load. Consequently, the guide shaft 16 can be made to move (slide) linearly in the axial direction.

Figure 7B:
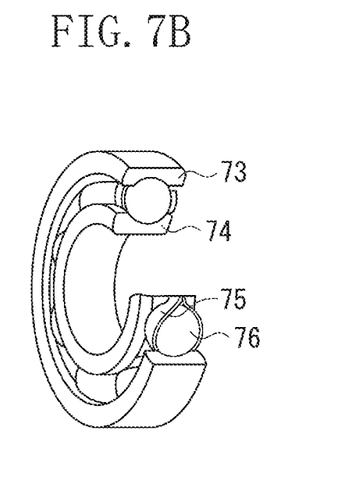

An example of the rolling bearing 42 according to the present exemplary embodiment will now be described with reference to FIG. 7B. A rolling bearing 42 is a bearing that rotates in the direction that intersects the axial direction of the guide shaft 16. A plurality of balls 76 is arranged between an outer race 73 called a "ball race" and an inner race 74. The plurality of balls 76 smoothly rolls while maintaining a constant interval due to a holding device 75 that prevents the balls from contacting each other.

As illustrated in FIG. 6A, there may be a gap between the guide shaft 16 and the linear motion bearing 41. In this case, for example, when the subject's eye is to be aligned with the ophthalmologic apparatus, the sliding substrate 11 can be moved in a lateral direction (axial direction of the guide shaft) with respect to the fixed base 10. In such a case, if the distance between the horizontal motion mechanism 15 (guide tube) and the center of gravity of the guide shaft 16 increases, the difference in the moments acting on the two ends of the guide shaft 16 increases. Consequently, the guide shaft 16 is more likely to incline with respect to the horizontal motion mechanism 15, and thus the sliding substrate 11 is more likely to lift up from the fixed base 10.

Further, in a case where the operator places his arm on the sliding substrate 11 in order to operate the operation stick positioned near the center of the guide shaft 16 of the sliding substrate 11, a moment difference relating to the weight of the operator's arm is produced. Consequently, the guide shaft 16 may become even more likely to incline with respect to the horizontal motion mechanism 15.

In a conventional ophthalmologic apparatus, the sliding substrate 11 and the measurement unit (housing) for measuring the subject's eye mounted on the sliding substrate 11 have generally been configured from a metal material. In such a case, even if a moment difference is produced at both ends of the guide shaft 16, these moments could be cancelled out by the weight of these parts. However, the measurement unit (housing) according to the present exemplary embodiment is, as described above, formed from a resin molded article in order to reduce the weight of the ophthalmologic apparatus 1. Consequently, the guide shaft 16 tends to incline with respect to the horizontal motion mechanism 15.

Figure 6B:
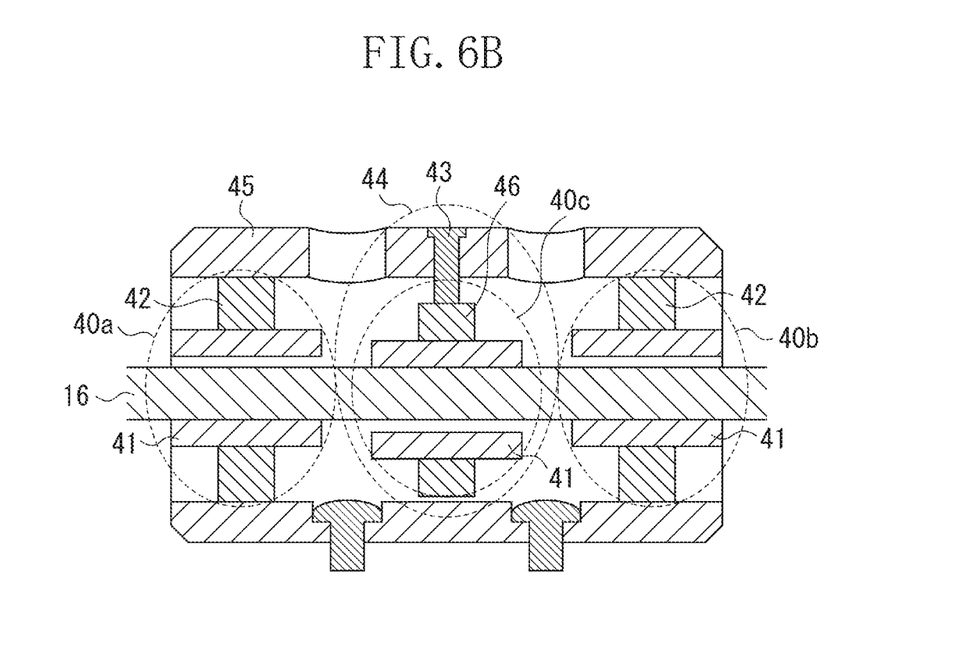
Figure 6C:
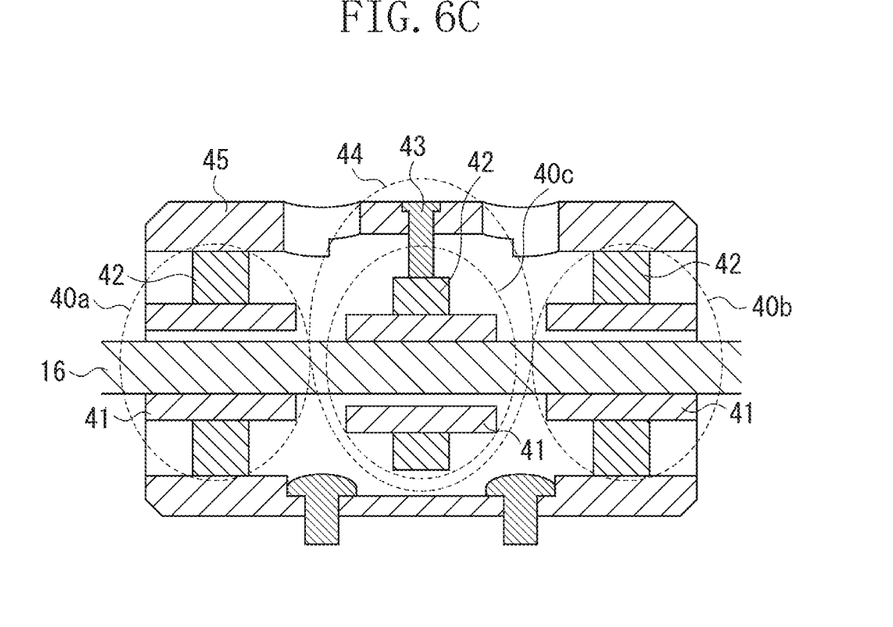

The configuration of the inclination reduction unit according to the present exemplary embodiment will now be described using FIGS. 6B and 6C. FIGS. 6B and 6C are cross-sectional views illustrating the inclination reduction unit according to the present exemplary embodiment.

A suppression mechanism 44 (an example of the inclination reduction unit for reducing inclination) for suppressing inclination (uplift) of the guide shaft 16 with respect to the fixed base 10 is provided between a plurality of shaft guide members 40a and 40b (an intermediate position is desirable).

In FIG. 6B, the suppression mechanism 44 has a shaft guide member 40c (also referred to as a "second shaft guide unit") that includes a linear motion bearing 41 and a rolling bearing 46 (that is smaller than the rolling bearing 42) provided on the outer periphery of the linear motion bearing 41. The suppression mechanism 44 also has a screw member 43 (an example of a pressing member that presses the second shaft guide unit on the guide shaft) that is screwed into the storage unit 45. The screw member 43 is made to abut the shaft guide member 40c by adjusting the rotation amount of the screw member 43. Specifically, to make the screw member 43 reliably abut the shaft guide member 40c, a force is applied on the shaft guide member 40c by rotating the screw member 43 with a slight torque. In this case, the shaft guide member 40c is eccentrically arranged with respect to the center axis of the plurality of shaft guide members 40a and 40b. This can be achieved by moving the shaft guide member 40c either up or down with respect to the plurality of shaft guide members 40a and 40b, which allows the inclination of the guide shaft 16 with respect to the fixed base 10 to be suppressed. Further, as illustrated in FIG. 6C, the rolling bearing 42 may be employed instead of the rolling bearing 46. In this case, it is desirable to cut off a part of the portion corresponding to the suppression mechanism 44 of the storage unit 45. Consequently, the above eccentric alignment can be reliably achieved without the rolling bearing 42 contacting the storage unit 45.

The shaft guide members 40a, 40b, and 40c are positioned at a predetermined position in the storage unit 45 by a (not illustrated) positioning member. Further, a spring member can also be employed for the suppression mechanism 44 instead of a screw member. A ball plunger can be employed as the spring member.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2011-167056 filed Jul. 29, 2011, which is hereby incorporated by reference herein in its entirety.

What is claimed is:
1. An ophthalmologic apparatus comprising:
   a measurement unit configured to measure a subject's eye;
   a sliding substrate configured to slide the measurement unit with respect to a base via a guide shaft;
   a plurality of shaft guide members provided on the base and configured to guide the guide shaft in an axial direction thereof; and
   an inclination reduction unit provided between the plurality of shaft guide members and configured to reduce inclination of the guide shaft with respect to the base.

2. The ophthalmologic apparatus according to claim 1, wherein the inclination of the guide shaft occurs in a case where the guide shaft is moved in the axial direction with respect to the plurality of shaft guide members.

3. The ophthalmologic apparatus according to claim 1, further comprising an operation stick provided on the sliding substrate,
   wherein the guide shaft moves with respect to the base in response to an operation of the operation stick.

4. The ophthalmologic apparatus according to claim 3, wherein the guide shaft moves in the axial direction with respect to the plurality of shaft guide members in response to an operation of the operation stick in an X direction.

5. The ophthalmologic apparatus according to claim 3, wherein the sliding substrate moves in a direction that intersects the axial direction of the guide shaft with respect to the base in response to an operation of the operation stick in a Z direction.

6. The ophthalmologic apparatus according to claim 1, further comprising:
   a rack mechanism provided on the sliding substrate; and
   a pinion mechanism provided on either end of the guide shaft and configured to engage the rack mechanism,
   wherein the sliding substrate moves in a direction in which a rack of the rack mechanism extends with respect to the base.

7. The ophthalmologic apparatus according to claim 1, wherein the plurality of shaft guide members constitutes a first shaft guide unit, and
   wherein the inclination reduction unit includes:
      a second shaft guide unit provided inside the first shaft guide unit; and
      a pressing member configured to press the second shaft guide unit against the guide shaft.

8. The ophthalmologic apparatus according to claim 7, wherein the pressing member presses the second shaft guide unit against the guide shaft so that the second shaft guide unit is eccentrically arranged with respect to a center axis of the first shaft guide unit.

9. The ophthalmologic apparatus according to claim 7, further comprising a storage unit configured to store the plurality of shaft guide members,
   wherein the plurality of shaft guide members and the inclination reduction unit are provided on the base via the storage unit, and
   wherein the pressing member is configured to press the second shaft guide unit against the guide shaft via the storage unit.

10. The ophthalmologic apparatus according to claim 7, wherein the pressing member includes a screw member, and wherein the screw member is configured to abut the second shaft guide unit with a rotation amount of the screw member adjusted.

11. The ophthalmologic apparatus according to claim 1, wherein the plurality of shaft guide members includes a plurality of linear motion bearings configured to guide the guide shaft in the axial direction, and
   wherein the ophthalmologic apparatus further comprises a plurality of rolling bearings provided on an outer periphery of the respective plurality of linear motion bearings.

12. An ophthalmologic apparatus comprising:
   a measurement unit configured to measure a subject's eye;
   a sliding substrate configured to slide the measurement unit with respect to a base via a guide shaft;
   a first shaft guide unit provided on the base and including a plurality of shaft guide members configured to guide the guide shaft in an axial direction thereof; and
   a second shaft guide unit provided inside the first shaft guide unit; and
   a pressing member configured to press the second shaft guide unit against the guide shaft.

13. The ophthalmologic apparatus according to claim 12, wherein the pressing member presses the second shaft guide unit against the guide shaft so that the second shaft guide unit is eccentrically arranged with respect to a center axis of the first shaft guide unit.

14. The ophthalmologic apparatus according to claim 12, further comprising a storage unit configured to store the plurality of shaft guide members,
   wherein the first shaft guide unit, the second shaft guide unit, and the pressing member are provided on the base via the storage unit, and
   wherein the pressing member is configured to press the second shaft guide unit against the guide shaft via the storage unit.

* * * * *